(12) United States Patent
Jaeschke et al.

(10) Patent No.: US 12,195,413 B2
(45) Date of Patent: *Jan. 14, 2025

(54) ETHYNYL DERIVATIVES

(71) Applicant: Hoffmann-La Roche Inc., Little Falls, NJ (US)

(72) Inventors: Georg Jaeschke, Basel (CH); Lothar Lindemann, Basel (CH); Antonio Ricci, Biel-Benken (CH); Eric Vieira, Frenkendorf (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 506 days.

This patent is subject to a terminal disclaimer.

(21) Appl. No.: 17/338,643

(22) Filed: Jun. 3, 2021

(65) Prior Publication Data
US 2021/0300844 A1  Sep. 30, 2021

Related U.S. Application Data

(63) Continuation of application No. 15/829,481, filed on Dec. 1, 2017, now Pat. No. 11,059,766, which is a (Continued)

(30) Foreign Application Priority Data
Jun. 3, 2015 (EP) ..................... 15170401

(51) Int. Cl.
| | | |
|---|---|---|
| *C07C 11/22* | (2006.01) | |
| *A61K 31/4166* | (2006.01) | |
| *A61K 31/4184* | (2006.01) | |
| *A61K 31/44* | (2006.01) | |
| *A61K 31/4439* | (2006.01) | |
| *A61P 1/00* | (2006.01) | |
| *A61P 1/04* | (2006.01) | |
| *A61P 25/00* | (2006.01) | |
| *A61P 25/04* | (2006.01) | |
| *A61P 25/16* | (2006.01) | |
| *A61P 25/18* | (2006.01) | |
| *A61P 25/22* | (2006.01) | |
| *A61P 25/24* | (2006.01) | |
| *A61P 25/28* | (2006.01) | |
| *A61P 29/00* | (2006.01) | |
| *A61P 43/00* | (2006.01) | |

(Continued)

(52) U.S. Cl.
CPC .......... *C07C 11/22* (2013.01); *A61K 31/4166* (2013.01); *A61K 31/4184* (2013.01); *A61K 31/44* (2013.01); *C07D 213/81* (2013.01); *C07D 401/04* (2013.01); *C07D 403/04* (2013.01); *A61K 2300/00* (2013.01)

(58) Field of Classification Search
CPC . C07C 11/22; A61K 31/4166; A61K 31/4184; A61K 31/44; A61K 2300/00; A61K 31/4439; C07D 213/81; C07D 401/04; C07D 403/04; A61P 1/00; A61P 1/04; A61P 25/00; A61P 25/04; A61P 25/16; A61P 25/18; A61P 25/22; A61P 25/24; A61P 25/28; A61P 29/00; A61P 43/00
See application file for complete search history.

(56) References Cited

U.S. PATENT DOCUMENTS

| | | |
|---|---|---|
| 3,549,655 A | 12/1970 | Bublitz et al. |
| 4,886,817 A | 12/1989 | Takeda et al. |
| | (Continued) | |

FOREIGN PATENT DOCUMENTS

| | | |
|---|---|---|
| CL | 200601797 A1 | 2/2007 |
| EA | 013013 B1 | 2/2010 |
| | (Continued) | |

OTHER PUBLICATIONS

Alagille, D. et al., "Synthesis and receptor assay of aromatic-ethynyl-aromatic derivatives with potent mGluR5 antagonist activity" Bioorg Med Chem 13(1):197-209 (Jan. 3, 2005).

(Continued)

*Primary Examiner* — Amanda L. Aguirre
*Assistant Examiner* — Sagar Patel

(57) ABSTRACT

The present invention relates to ethynyl derivatives of formula I

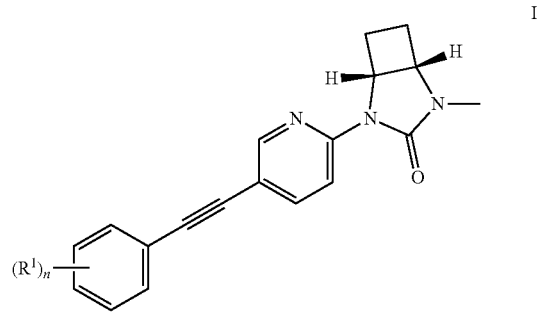

with variables as defined herein, or to a pharmaceutically acceptable acid addition salt thereof Compounds of formula I are metabotropic glutamate receptor antagonists (negative allosteric modulators) for use in the treatment of, e.g., anxiety and pain, depression, Fragile-X syndrome, autism spectrum disorders, Parkinson's disease, and gastroesophageal reflux disease (GERD).

15 Claims, 2 Drawing Sheets

Related U.S. Application Data continuation of application No. PCT/EP2016/062202, filed on May 31, 2016.

(51) Int. Cl.
*C07D 213/81* (2006.01)
*C07D 401/04* (2006.01)
*C07D 403/04* (2006.01)

(56) References Cited

U.S. PATENT DOCUMENTS

| | | | |
|---|---|---|---|
| 6,599,917 | B1 | 7/2003 | Okada. et al. |
| 7,112,593 | B2 | 9/2006 | Okada et al. |
| 8,034,806 | B2 | 10/2011 | Conn et al. |
| 8,420,661 | B2 * | 4/2013 | Green ............... C07D 401/04 |
| | | | 514/278 |
| 8,513,273 | B2 | 8/2013 | Green et al. |
| 8,618,296 | B2 | 12/2013 | Green et al. |
| 8,648,088 | B2 | 2/2014 | Jaeschke et al. |
| 8,716,316 | B2 | 5/2014 | Green et al. |
| 8,969,338 | B2 | 3/2015 | Jaeschke et al. |
| 9,199,971 | B2 | 12/2015 | Jaeschke et al. |
| 9,221,802 | B2 | 12/2015 | Jaeschke et al. |
| 9,315,498 | B2 | 4/2016 | Green et al. |
| 9,328,090 | B2 | 5/2016 | Jaeschke et al. |
| 9,359,301 | B2 | 6/2016 | Jaeschke et al. |
| 9,682,959 | B2 | 6/2017 | Jaeschke et al. |
| 9,751,856 | B2 | 9/2017 | Jaeschke et al. |
| 2007/0105899 | A1 | 5/2007 | Suzuki et al. |
| 2009/0042855 | A1 | 2/2009 | Conn et al. |
| 2009/0270362 | A1 | 10/2009 | Conn et al. |
| 2010/0179161 | A1 | 7/2010 | Shankar et al. |
| 2013/0090332 | A1 | 4/2013 | Lindemann et al. |
| 2014/0155602 | A1 | 6/2014 | Green et al. |

FOREIGN PATENT DOCUMENTS

| | | |
|---|---|---|
| JP | H07-181440 A | 7/1995 |
| JP | H09-151179 A | 6/1997 |
| JP | 2004-517947 A | 6/2004 |
| JP | 2014-512401 A | 5/2014 |
| JP | 2014-514315 A | 6/2014 |
| KR | 10-1431367 B1 | 8/2014 |
| WO | 1996/037466 A1 | 11/1996 |
| WO | 2000/20001 A1 | 4/2000 |
| WO | 01/16121 A1 | 3/2001 |
| WO | 2002/14517 A1 | 2/2002 |
| WO | 02/18353 A2 | 3/2002 |
| WO | 02/062323 A2 | 8/2002 |
| WO | 2002/078745 A2 | 10/2002 |
| WO | 2004/038374 A2 | 5/2004 |
| WO | 2004/039780 A1 | 5/2004 |
| WO | 2005/044797 A1 | 6/2004 |
| WO | 2005/094822 A1 | 10/2005 |
| WO | 2005/108370 | 11/2005 |
| WO | 2006/048771 A1 | 5/2006 |
| WO | 2006/129199 A1 | 12/2006 |
| WO | 2007/006530 A1 | 1/2007 |
| WO | 2007/035823 A2 | 3/2007 |
| WO | 2007/050050 A2 | 5/2007 |
| WO | 2008/151184 A1 | 12/2008 |
| WO | 2009/098208 A1 | 8/2009 |
| WO | 2010/063487 A1 | 6/2010 |
| WO | 2011/015343 A1 | 2/2011 |
| WO | 2011/051201 A1 | 5/2011 |
| WO | 2011/073172 | 6/2011 |
| WO | 2011/128279 A1 | 10/2011 |
| WO | 2012/004400 A1 | 1/2012 |
| WO | 2012/015024 | 2/2012 |
| WO | 2012/064603 A1 | 5/2012 |
| WO | 2012/143340 A1 | 10/2012 |
| WO | 2012/146551 A1 | 11/2012 |
| WO | 2012/146552 A1 | 11/2012 |
| WO | 2013/045380 A2 | 4/2013 |
| WO | 2013/050454 A1 | 4/2013 |
| WO | 2013/050460 A1 | 4/2013 |
| WO | 2013-523854 A | 4/2013 |
| WO | 2014/012851 A1 | 1/2014 |
| WO | 2014/026880 A1 | 2/2014 |
| WO | 2014/056710 A1 | 4/2014 |
| WO | 2014/060384 A1 | 4/2014 |
| WO | 2014/060398 A1 | 4/2014 |
| WO | 2015/004007 A1 | 1/2015 |
| WO | 2015/128307 A1 | 9/2015 |

OTHER PUBLICATIONS

Alagille, D., et al., "Potent mGluR5 antagonists: Pyridyl and thiazolyl-ethynyl-3,5-disubstituted-phenyl series" Bioorg Med Chem Lett 21(11):3243-3247 (Apr. 12, 2011).
Bach, P., et al., "Metabotropic glutamate receptor 5 modulators and their potential therapeutic applications" Expert Opin Therap Patents 17(4):371-384 (Apr. 19, 2007).
Barbaud, C., et al., "Synthesis of novel α,α',β-trisubstituted β-lactones" Tetrahedron Letters 43(52):9513-9515 (Dec. 23, 2002).
Boer, K., et al., "Cellular localization of metabotropic glutamate receptors in cortical tubers and subependymal giant cell tumors of tuberous sclerosis complex." Neuroscience 156(1):203-215 (Sep. 22, 2008).
Chua, P., et al., "Cyclohexenyl- and dehydropiperidinyl-alkynyl pyridines as potent metabotropic glutamate subtype 5 (mGlu5) receptor antagonists" Bioorg Med Chem Lett 15(20):4589-4593 (Sep. 15, 2005).
Written Opinion of the International Searching Authority for PCT/EP2013/064747.
Damasio, A., "Alzheimer's Disease and Related Dementias" Cecil Textbook of Medicine 20(2):1992-1996 (Jan. 1, 1996).
Gasparini, F., et al., "Allosteric Modulators for mGlu Receptors" Curr Neuropharmacol 5(3):187-194 (Sep. 1, 2007).
Gorrea, E., et al., "Synthesis and structural features of cyclobutane-containing chiral bicyclic ureas, Tetrahedron" Tetrahedron: Asymmetry 21(3):339-345 (Mar. 1, 2010).
Gross, C. et al., "Therapeutic strategies in fragile X syndrome: dysregulated mGluR signaling and beyond." Neuropsychopharmacology [Nature] 37(1):178-195 (Jan. 1, 2012).
ISR and Written Opinion for PCT/EP2011/055585:pp. 1-4 (Oct. 20, 2011).
ISR and Written opinion for PCT/EP2012/057336:pp. 1-4 (May 30, 2012).
ISR & WO for PCT/EP2013/066443.
ISR & WO for PCT/EP2013/069674.
ISR for PCT/EP2013/064747.
ISR and Written Opinion for PCT/EP2012/069599 Nov. 15, 2012.
ISR of PCT/EP2016/062202 (Aug. 17, 2016).
Kinney, G., et al., "A Novel Selective Positive Allosteric Modulator of Metabotropic Glutamate Receptor Subtype 5 Has in Vivo Activity and Antipsychotic-Like Effects in Rat Behavioral Models" J Pharmacol Exp Ther 313(1):199-206 (Apr. 1, 2005).
Krueger, D., et al., "Toward fulfilling the promise of molecular medicine in fragile X syndrome." Annu Rev Med 18(62):411-419 (Feb. 18, 2011).
Layzer, R., "Section Five: Degenerative Diseases of the Nervous System" Cecil Textbook of Medicine 20(2):2050-2057 (Jan. 1, 1996).
Lynch, G., "Novel therapies for sarcopenia: ameliorating age-related changes in skeletal muscle" Expert Opin Therap Patents 12(1):11-27 (Feb. 25, 2002).
Lysenko, I.L., et al., "A Convenient Procedure for Preparation of 1-(1-Aminoalkyl)-1-cyclopropanols from N-Benzyl α-Amino Acid Esters" Russian J Org Chem 37(9):1238-1243 (Sep. 1, 2001).
Mutel, V.,, "Therapeutic potential of non-competitive, subtype-selective metabotropic glutamate receptor ligands" Expert Opin on Therap Patents 12(12):1845-1852 (Feb. 25, 2002).
Owen, D.R.J., et al., "Imaging of Atherosclerosis" Annu Rev Med 62:25-40 (Feb. 1, 2011).

(56) References Cited

OTHER PUBLICATIONS

Rocher et al., "mGluR5 Negative Allosteric Modulators Overview: A Medicinal Chemistry Approach Towards a Series of Novel Therapeutic Agents" Current Topics in Medicinal Chemistry 11:680-695 (2001).

Rodriguez, A., et al., "Discovery of Novel Allosteric Modulators of Metabotropic Glutamate Receptor Subtype 5 Reveals Chemical and Functional Diversity and In Vivo Activity in Rat Behavioral Models of Anxiolytic and Antipsychotic Activity" Mol Pharmacol 78(6):1105-1123 (Dec. 1, 2010).

Son, M.H., et al., "Synthesis and biological evaluation of 2-(arylethynl)quinoline derivatives as mGluR5 antagonists for the treatment of neuropathic pain" Bioorg Med Chem Lett 23(5):1472-1476 (Mar. 1, 2013).

The English translation of Japanese Office action, issued Jan. 28, 2014, in the corresponding Japanese Application No. 2013-504215.

The English translation of the Taiwanese Office Action, issued on Dec. 25, 2013, in the corresponding Tawainese Application No. 101136749.

Translation of Taiwanese Off Act. In Corres Taiwan App 100112500 Jan. 16, 2013.

Wu, F.S., et al., "Pregnenolone sulfate: a positive allosteric modulator at the N-methyl-D-aspartate receptor." Mol Pharmacol 40(3):333-336 (Sep. 1, 1991).

\* cited by examiner

ETHYNYL DERIVATIVES

CROSS-REFERENCE TO RELATED APPLICATIONS

This application is a continuation application of U.S. patent application Ser. No. 15/829,481, filed on Dec. 1, 2017, which is a continuation application of International Patent Application No. PCT/EP2016/062202, filed on May 31, 2016, which claims the benefit of priority to European Patent Application 15170401.2, filed on Jun. 3, 2015, each of which is incorporated herein by reference in its entirety.

The present invention relates to ethynyl derivatives of formula I

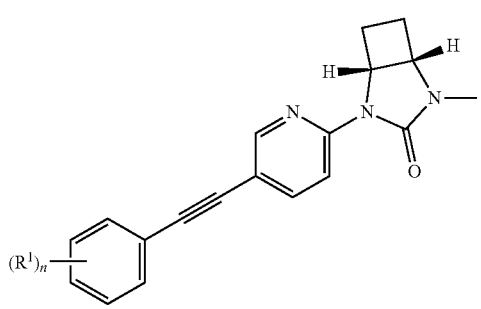

wherein
$R^1$ is hydrogen or F;
n is 1 or 2
or to a pharmaceutically acceptable acid addition salt thereof.

Preferred compounds are those wherein $(R^1)_n$ is hydrogen, 3-fluoro, 4-fluoro or 2,5-difluoro.

One embodiment of the present invention are compounds of formula I, for example the following:
(1S,5R)-2-methyl-4-(5-(phenylethynyl)pyridin-2-yl)-2,4-diazabicyclo[3.2.0]heptan-3-one
(1R,5S)-2-(5-((4-fluorophenyl)ethynyl)pyridin-2-yl)-4-methyl-2,4-diazabicyclo[3.2.0]heptan-3-one
(1R,5S)-2-(5-((3-fluorophenyl)ethynyl)pyridin-2-yl)-4-methyl-2,4-diazabicyclo[3.2.0]heptan-3-one or
(1R,5S)-2-(5-((2,5-difluorophenyl)ethynyl)pyridin-2-yl)-4-methyl-2,4-diazabicyclo[3.2.0]heptan-3-one.
Other embodiments are described herein.

It has now surprisingly been found that the compounds of general formula I are metabotropic glutamate receptor antagonists (NAM=negative allosteric modulators). Compounds with a similar main core have been generically described as positive allosteric modulators of the mGluR5 receptor. Surprisingly, it has been found that highly potent mGluR5 antagonists were obtained instead of mGluR5 positive allosteric modulators, which have a completely opposite pharmacology if compared with positive allosteric modulators.

A mGluR5 positive allosteric modulator (PAM) leads to increased receptor activity ($Ca^{2+}$ mobilization) in presence of a fixed concentration of glutamate, whereas an allosteric antagonist (negative allosteric modulator, NAM) leads to a reduction of receptor activation.

Compounds of formula I are distinguished by having valuable therapeutic properties. They can be used in the treatment of anxiety and pain, depression, Fragile-X syndrome, autism spectrum disorders, Parkinson's disease, and gastroesophageal reflux disease (GERD).

In the central nervous system (CNS) the transmission of stimuli takes place by the interaction of a neurotransmitter, which is sent out by a neuron, with a neuro-receptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Negative allosteric modulators of metabotropic glutamate receptors, belonging to the first group, can be used for the treatment or prevention of acute and/or chronic neurological disorders such as Parkinson's disease, Fragile-X syndrome, autistic disorders, cognitive disorders and memory deficits, as well as chronic and acute pain and gastro-esophageal reflux disease (GERD).

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

Selective mGluR5 antagonists are especially useful for the treatment of disorders where reduction of mGluR5 receptor activation is desired, such as anxiety and pain, depression, Fragile-X syndrome, autism spectrum disorders, Parkinson's disease, and gastroesophageal reflux disease (GERD).

Objects of the present invention include compounds of formula I and their pharmaceutically acceptable salts, the above-mentioned compounds as pharmaceutically active substances and their production. Further objects of the invention include medicaments based on a compound in accordance with the invention and their manufacture as well as the use of the compounds in the control or prevention of mGluR5 receptor (NAM) mediated disorders, which include anxiety and/or pain, depression, Fragile-X syndrome, autism spectrum disorders, Parkinson's disease, and gastro-esophageal reflux disease (GERD), and, respectively, for the production of corresponding medicaments.

Compounds of the present invention have been generically described in reference 1 (WO2011128279) as positive allosteric modulators of the mGluR5 receptor. Most similar exemplified compounds are linked to a 5- or 6-membered ring. Surprisingly it has been found that compounds having a smaller ring size, a 4-membered ring, and with the absolute stereochemistry of the bicyclic ring (1R,5S), are highly potent mGluR5 antagonists, which have a completely opposite pharmacology to that described in WO2011128279 for positive allosteric modulators.

The main difference between positive- and negative allosteric modulators can be seen in FIG. 1. An mGluR5 positive allosteric modulator (PAM) leads to increased receptor activity ($Ca^{2+}$ mobilisation) in presence of a fixed concentration of glutamate whereas an allosteric antagonist (negative allosteric modulator, NAM) leads to a reduction of receptor activation. The affinity for the receptor in FIG. 1 is ca. $10^{-7}$ M for the PAM and between $10^{-7}$M and $10^{-8}$ M for the NAM. These values can also be measured using a binding assay to displace a radioligand (=MPEP) see assay description.

Pharmaceutically acceptable salts of compounds of formula I can be manufactured readily according to methods known per se and taking into consideration the nature of the compound to be converted into a salt. Inorganic or organic acids such as, for example, hydrochloric acid, hydro-bromic acid, sulphuric acid, nitric acid, phosphoric acid or citric acid, formic acid, fumaric acid, maleic acid, acetic acid, succinic acid, tartaric acid, methane sulphonic acid, p-toluene sulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, metabotropic glutamate receptor antagonists and can be used for the treatment or prevention of mGluR5 receptor mediated disorders, such as acute and/or chronic neurological disorders, cognitive disorders and memory deficits, as well as acute and chronic pain. Treatable neurological disorders are for instance epilepsy, schizophrenia, anxiety, acute, traumatic or chronic degenerative processes of the nervous system, such as Alzheimer's disease, senile dementia, Huntington's chorea, ALS, multiple sclerosis, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression. Other treatable indications are restricted brain function caused by bypass operations or transplants, poor blood supply to the brain, spinal cord injuries, head injuries, hypoxia caused by pregnancy, cardiac arrest and hypoglycaemia.

The compounds of formula I and their pharmaceutically acceptable salts are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or biliary colic, menstruation, migraine and gout.

The compounds of formula I and pharmaceutically acceptable salts thereof can be used as medicaments, e.g., in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula I or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01-10 mg/kg/day, with a dosage of 0.1-5 mg/kg/day being preferred for all of the indications described. The daily dosage for an adult human being weighing 70 kg accordingly lies between 0.7-700 mg per day, preferably between 7 and 350 mg per day.

EXAMPLES mGluR5-NAMs are beneficial for indications where a reduction of excessive receptor activity is desired, such as anxiety, pain, Fragile-X, autism spectrum disorders, and gastroeosophagal reflux disease. mGluR5 PAMs on the other hand are useful in indications where a normalisation of decreased receptor activity is desired such as in psychosis, epilepsy, schizophrenia, Alzheimer's disease and associated cognitive disorders, as well as tuberous sclerosis.

Figure 1:
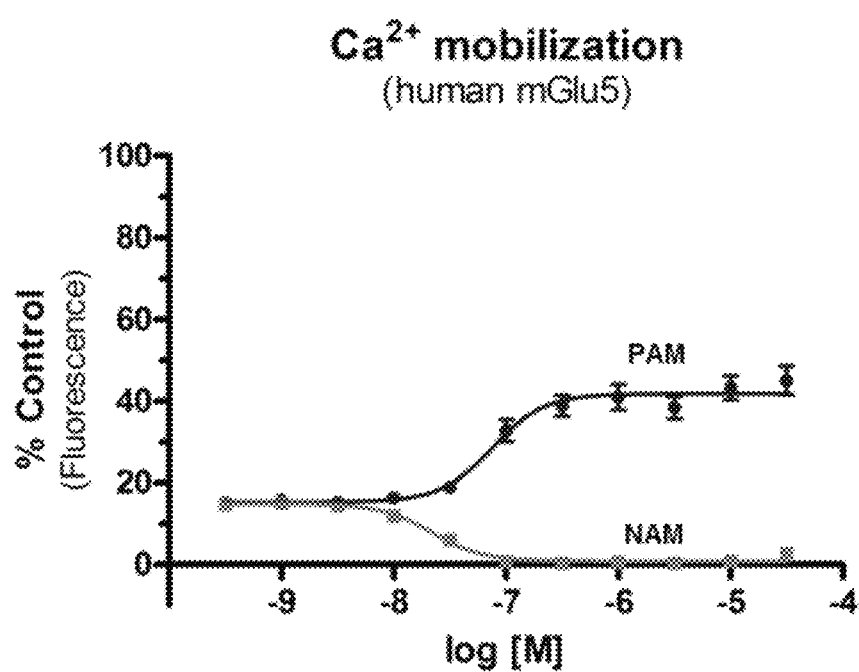
FIG. 1: Comparison of an mGluR5 positive allosteric modulator (PAM) and an mGluR5 antagonist (negative allosteric modulator=NAM)
Figure 2:
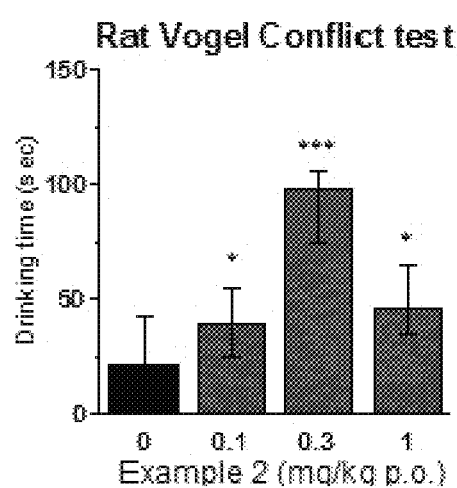
FIG. 2: Activity of compound "Example 2" in the rat Vogel conflict drinking test.

This difference can be practically shown for example in an anxiety animal model such as the rat Vogel conflict drinking test where the compound of Example 1 shows anxiolytic activity at a minimal effective dose of 0.1 mg/Kg whereas mGluR-PAMs are not expected to show activity in this animal model (see FIG. 2).

Biological Assays and Data

Intracellular $Ca^{2+}$ Mobilization Assay

A monoclonal HEK-293 cell line stably transfected with a cDNA encoding for the human mGlu5a receptor was generated; for the work with mGlu5 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 μg/ml hygromycin and 15 m/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 μM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min with on-line recording of fluorescence. Following this pre-incubation step, the agonist L-glutamate was added to the cells at a concentration corresponding to $EC_{20}$ (typically around 80 μM) with on-line recording of fluorescence; in order to account for day-to-day variations in the responsiveness of cells, the $EC_{20}$ of glutamate was determined immediately ahead of each experiment by recording of a full dose-response curve of glutamate.

Responses were measured as peak increase in fluorescence minus basal (i.e. fluorescence without addition of L-glutamate), normalized to the maximal stimulatory effect obtained with saturating concentrations of L-glutamate. Graphs were plotted with the % maximal stimulatory using XLfit, a curve fitting program that iteratively plots the data using Levenburg Marquardt algorithm. The single site competition analysis equation used was y=A+((B−A)/(1+((x/C)D))), where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (concentration at which half maximal stimulation was achieved), the Hill coefficient as well as the maximal response in % of the maximal stimulatory effect obtained with saturating concentrations of L-glutamate were calculated.

Positive signals obtained during the pre-incubation with the PAM test compounds (i.e. before application of an $EC_{20}$ concentration of L-glutamate) were indicative of an agonistic activity, the absence of such signals were demonstrating the lack of agonistic activities. A depression of the signal observed after addition of the $EC_{20}$ concentration of L-glutamate was indicative of an inhibitory activity of the test compound.

In the list of examples below are shown the corresponding results for compounds which all have $EC_{50}$ values less or equal 100 nM.

WO2011128279=Ref 1

| Example | mGlu5 PAM $EC_{50}$ [nM] | Efficacy [%] |
|---|---|---|
| Ref. 1; Ex. 106 | 30 | 42 |
| Ref. 1; Ex. 109 | 18 | 37 |
| Ex. 1 | inactive | |
| Ex. 2 | inactive | |
| Ex. 3 | inactive | |
| Ex. 4 | inactive | |

MPEP Binding Assay

For binding experiments, cDNA encoding human mGlu 5a receptor was transiently transfected into EBNA cells using a procedure described by Schlaeger and Christensen [Cytotechnology 15:1-13 (1998)]. Cell membrane homogenates were stored at −80° C. until the day of assay where upon they were thawed and resuspended and polytronised in 15 mM Tris-HCl, 120 mM NaCl, 100 mM KCl, 25 mM $CaCl_2$, 25 mM $MgCl_2$ binding buffer at pH 7.4 to a final assay concentration of 20 μg protein/well.

Saturation isotherms were determined by addition of twelve [$^3$H]MPEP concentrations (0.04-100 nM) to these membranes (in a total volume of 200 μl) for 1 h at 4° C. Competition experiments were performed with a fixed concentration of [$^3$H]MPEP (2 nM) and $IC_{50}$ values of test compounds evaluated using 11 concentrations (0.3-10,000 nM). Incubations were performed for 1 h at 4° C.

At the end of the incubation, membranes were filtered onto unifilter (96-well white microplate with bonded GF/C filter preincubated 1 h in 0.1% PEI in wash buffer, Packard BioScience, Meriden, Conn.) with a Filtermate 96 harvester (Packard BioScience) and washed 3 times with cold 50 mM Tris-HCl, pH 7.4 buffer. Nonspecific binding was measured in the presence of 10 μM MPEP. The radioactivity on the filter was counted (3 min) on a Packard Top-count microplate scintillation counter with quenching correction after addition of 45 μl of microscint 40 (Canberra Packard S.A., Zurich, Switzerland) and shaking for 20 min.

In the list of examples below are shown the corresponding results for compounds which all have $EC_{50}$ values less or equal to 20 nM.

| Example | mGlu5-MPEP binding $EC_{50}$ (nM) |
|---|---|
| Ref. 1; Ex. 106 | 8 |
| Ref. 1; Ex. 109 | 12 |
| 1 | 9 |
| 2 | 5 |
| 3 | 4 |
| 4 | 3 |

Comparison of the compounds of the invention versus the most similar compounds described in WO2011128279, examples 106 and 109.

As can be seen in the table below, the compounds of the invention show a clearly different profile compared to structurally similar compounds of prior art which is an advantage when compounds showing NAM activity are desired.

| Ex. | Structure | EC$_{50}$ (nM) mGlu5 PAM assay | Ki (nM) MPEP binding | Activity profile |
|---|---|---|---|---|
| Ref. 1 Ex. 106 | 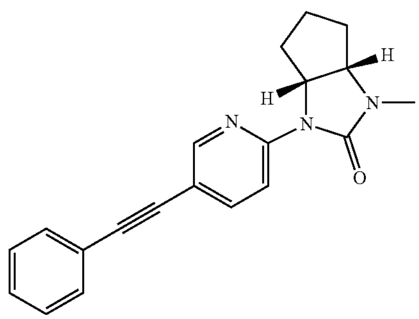 [SMILES: CN1C(=O)N(c2ccc(C#Cc3ccccc3)cn2)[C@@H]2CCC[C@@H]21] | 30 | 8 | PAM |
| Ref. 1 Ex. 109 | 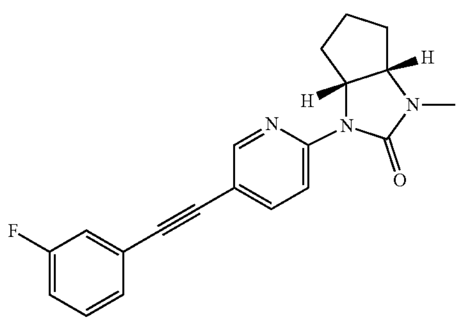 [SMILES: CN1C(=O)N(c2ccc(C#Cc3cccc(F)c3)cn2)[C@@H]2CCC[C@@H]21] | 18 | 37 | PAM |
| 1 | 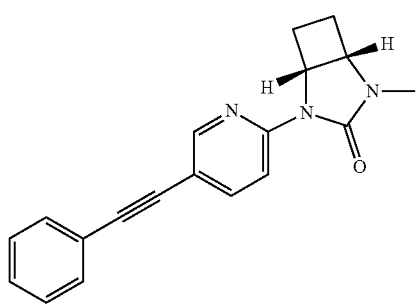 [SMILES: CN1C(=O)N(c2ccc(C#Cc3ccccc3)cn2)[C@@H]2CC[C@@H]21] | inactive | 9 | NAM |
| 2 | 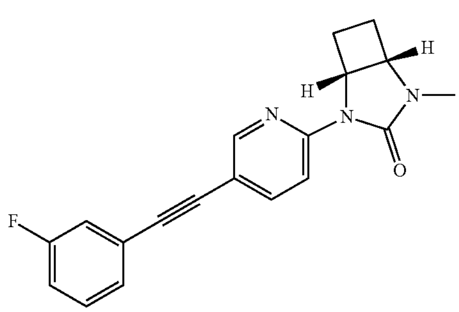 [SMILES: CN1C(=O)N(c2ccc(C#Cc3cccc(F)c3)cn2)[C@@H]2CC[C@@H]21] | inactive | 5 | NAM |

-continued

| Ex. | Structure | EC$_{50}$ (nM) mGlu5 PAM assay | Ki (nM) MPEP binding | Activity profile |
|---|---|---|---|---|
| 3 | 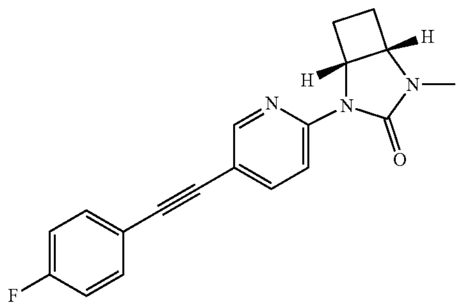 [SMILES: CN1C(=O)N(c2ccc(C#Cc3ccc(F)cc3)cn2)[C@@H]2CC[C@@H]21] | inactive | 4 | NAM |
| 4 | 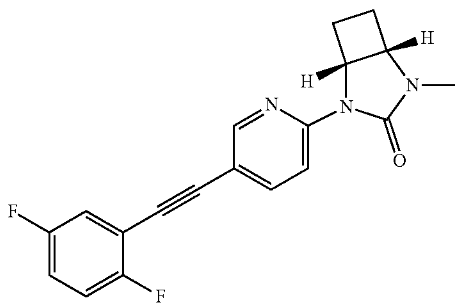 [SMILES: CN1C(=O)N(c2ccc(C#Cc3cc(F)ccc3F)cn2)[C@@H]2CC[C@@H]21] | inactive | 3 | NAM |

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts may be prepared by methods, known in the art, for example by the process variant described below, which process comprises reacting a compound of formula II

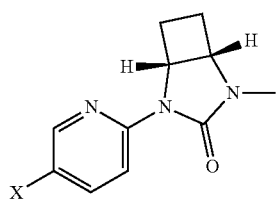

II wherein X is a halogen atom selected from bromine or iodine with a suitable aryl-acetylene of formula III

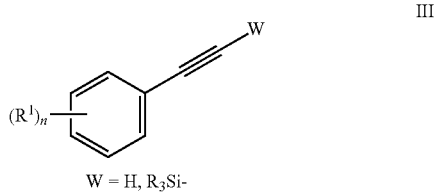

III

W = H, R$_3$Sito form a compound of formula I

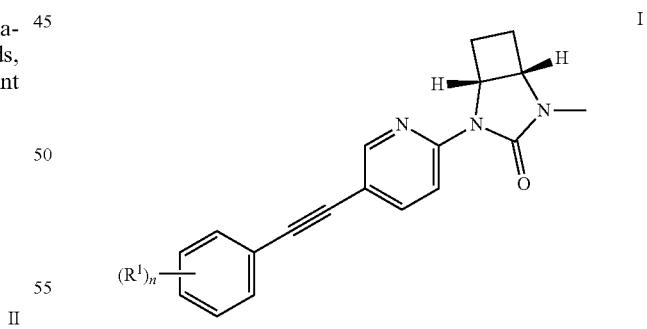

I wherein the substituent R$^1$ is described above, in enantiomerically pure form with the absolute stereochemistry as drawn in formula I or by using II in racemic form followed by chiral separation of I to yield the optically pure enantiomer; and if desired, converting the compounds obtained into pharmaceutically acceptable acid addition salts.

The preparation of compounds of formula I is further described in more detail in schemes 1 to 3 and in examples 1-4.

Scheme 1

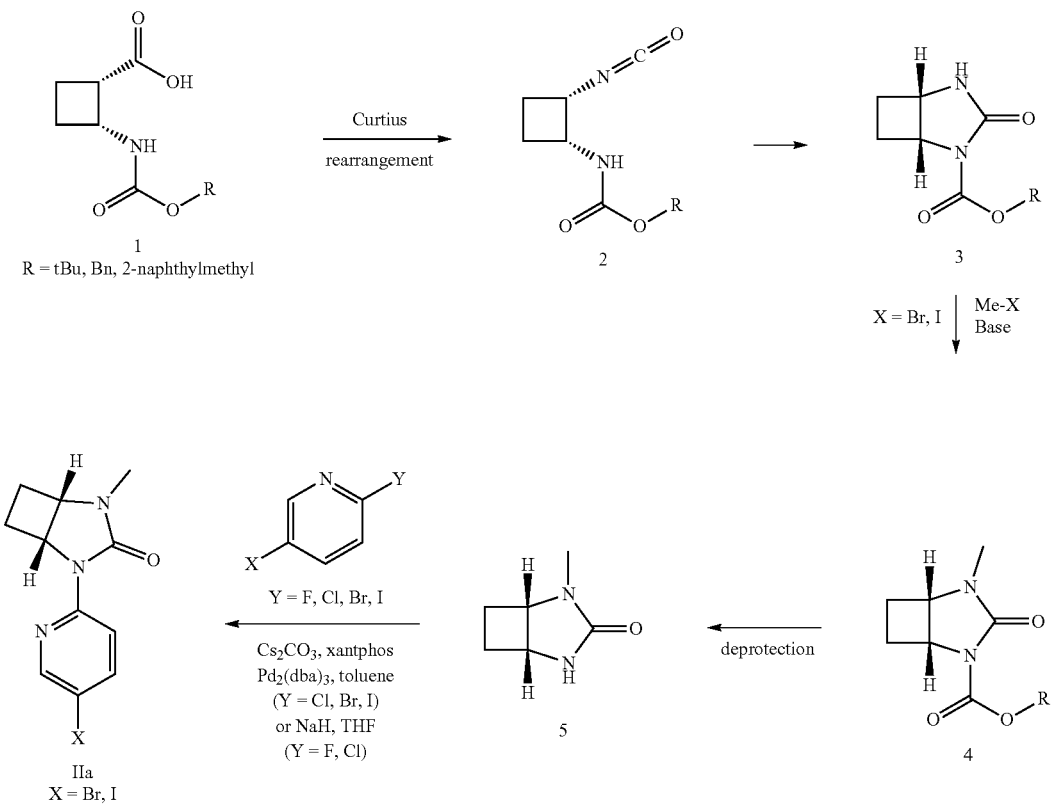

The synthesis of compounds of formula IIa is described in scheme 1. A halo-pyridine compound of formula IIa can be obtained by a Palladium catalyzed reaction of an appropriate dihalogenated pyridine such as 2-bromo-5-iodo-pyridine with an appropriately substituted cyclic urea of formula 5 (scheme 1). Reaction of a 2-chloro- or 2-fluoro-pyridine having a bromine or iodine in position 5 with a bicyclic urea of formula 5 can also form a compound of formula IIa by an aromatic nuclophilic substitution reaction using basic conditions such as for example NaH/THF or Cesium carbonate/DMF. The compound of formula 5 can be obtained starting from an appropriately protected 2-amino-1-carboxylic acid of formula 1 which can be obtained using procedures similar to those described by Gorrea & al., Tetrahedron Asymmetry, 21, 339 (2010). The acid function of 1 is transformed via an acylazide intermediate into the corresponding isocyanate 2 (Curtius rearrangement) which then cyclizes to form the bicyclic urea compound 3. The free NH group of 3 can be methylated according to standard procedures to form compound 4 which is then deprotected to yield the cyclic urea 5. It is also possible to obtain optically pure intermediates 2 to 5 starting from an optically pure protected acid of formula 1 or by separation of the racemic mixture at any stage of the synthesis using procedures known to persons skilled in the art.

Scheme 2

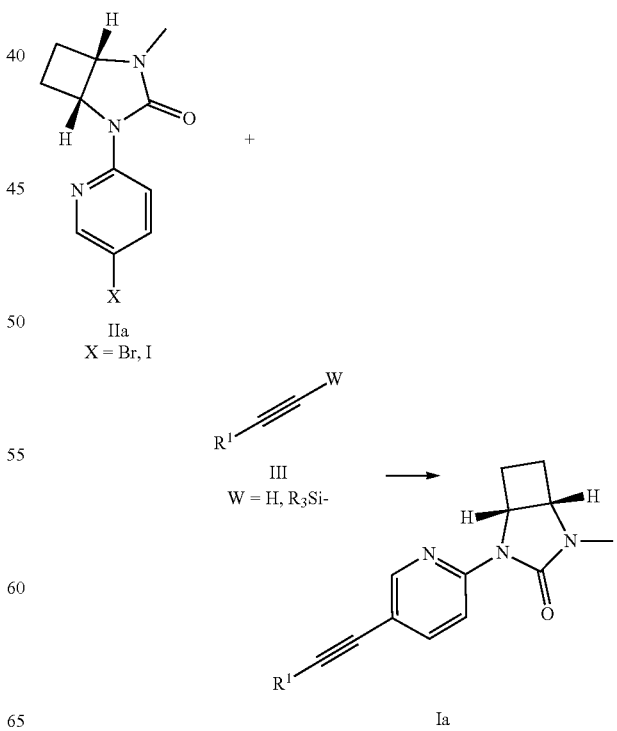

Wherein $R^1$ in this scheme means phenyl substituted by $(R^1)_n$.

The compound of formula IIa (X=Br, I) may react with a suitable aryl-acetylene of formula III (where W is either hydrogen or an in-situ cleavable protecting group such as a trialkylsilyl- or aryldialkylsilyl-group, preferably hydrogen or trimethylsilyl) under Palladium catalyzed coupling conditions (Sonogashira reaction) to form a compound of formula Ia, wherein the substituent $R^1$ is described above. Another possibility consists of reacting IIa with trimethylsilyl acetylene to yield a compound of formula Ia where $R^1$ is trimethylsilyl and then do a second Sonogashira reaction with an appropriate aryl bromide or aryl iodide to yield a compound of formula I (scheme not shown).

In the case where the amino acid derivative 1 is in racemic form, the enantiomers can be separated at any given stage during the synthesis of compounds of formula I using procedures known to persons skilled in the art.

It is also possible to invert the sequence of reactions leading to compounds of formula I (scheme 3). In this case, the Sonogashira reaction between the arylacetylene derivative III and the dihalo-pyridine is performed first to yield an arylacetylene-pyridine compound of formula 6 which is then condensed with the bicyclic urea 1 to yield compounds of formula I.

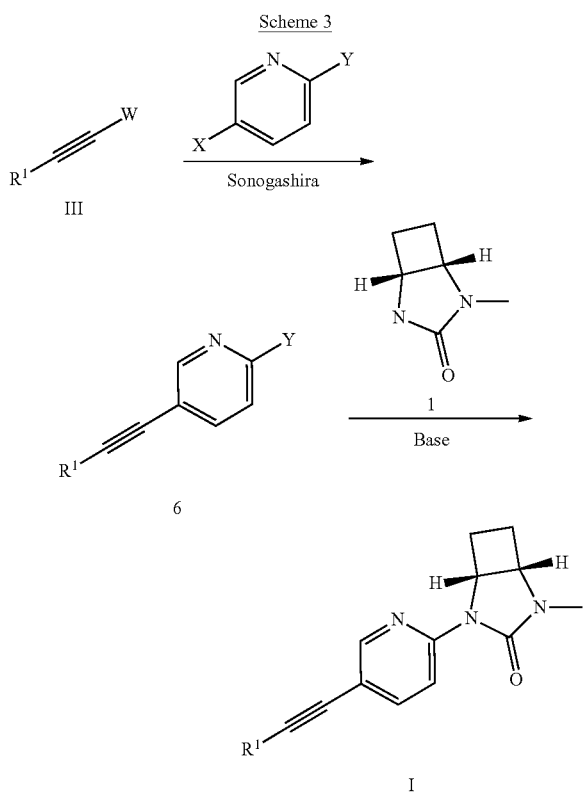

Scheme 3

Wherein $R^1$ in this scheme means phenyl substituted by $(On$.

The pharmacological activity of the compounds was tested using the following method:

cDNA encoding rat mGlu 5a receptor was transiently transfected into EBNA cells using a procedure described by E.-J. Schlaeger and K. Christensen (*Cytotechnology* 1998, 15, 1-13). [$Ca^{2+}$]i measurements were performed on mGlu 5a transfected EBNA cells after incubation of the cells with Fluo 3-AM (obtainable by FLUKA, 0.5 µM final concentration) for 1 hour at 37° C. followed by 4 washes with assay buffer (DMEM supplemented with Hank's salt and 20 mM HEPES. [$Ca^{2+}$]i measurements were done using a fluorometric imaging plate reader (FLIPR, Molecular Devices Corporation, La Jolla, Calif., USA). When compounds were evaluated as antagonists they were tested against 10 µM glutamate as agonist.

The inhibition (antagonists) curves were fitted with a four parameter logistic equation giving $IC_{50}$, and Hill coefficient using the iterative non-linear curve fitting software Origin (Microcal Software Inc., Northampton, Mass., USA).

The Ki values of the compounds tested are given. The Ki value is defined by the following formula:

$$K_i = \frac{IC_{50}}{1 + \frac{[L]}{EC_{50}}}$$

in which the $IC_{50}$ values are those concentrations of the compounds tested in µM by which 50% of the effect of compounds are antagonized. [L] is the concentration and the $EC_{50}$ value is the concentration of the compounds in µM which brings about 50% stimulation.

The compounds of the present invention are mGluR 5a receptor antagonists. The activities of compounds of formula I as measured in the assay described above are in the range of $K_i < 100$ µM.

SYNTHETIC EXAMPLES

Example 1

(−)-(1S,5R)-2-methyl-4-(5-(phenylethynyl)pyridin-2-yl)-2,4-diazabicyclo[3.2.0]heptan-3-one

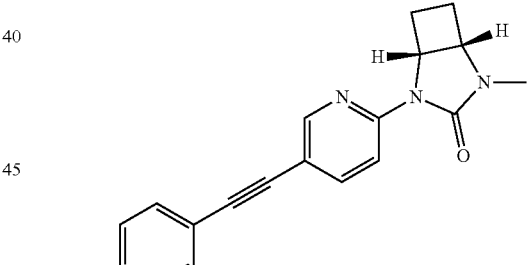

Step 1: (rac)-(1SR,2RS)-2-(Naphthalen-2-yl-methoxycarbonylamino)cyclobutanecarboxylic acid Methyl Ester To a well stirred solution of (rac)-(cis)-(1RS,2SR)-cyclobutane-1,2-dicarboxylic acid monomethyl ester (CAS: 31420-52-7) (10.8 g, 68.3 mmol), and N-methylmorpholine (7.6 g, 8.26 ml, 75.1 mmol) in 160 ml of 1,2-dichloroethane was added dropwise diphenylphosphoryl azide (20.7 g, 16.2 ml, 75.1 mmol). After stirring for 10 min at room temperature, the reaction was warmed to 60° C. 2-Naphthylmethyl alcohol (10.8 g, 68.3 mmol) and copper(I)chloride (68 mg, 0.68 mmol) were added and the reaction was stirred for another 16 h at 60° C. The reaction was concentrated in vaccuo, the light brown oily residue (51 g) was diluted with 15 ml of dichloromethane and purified by flash chromatography on silicagel (SiO$_2$ (650 g), Ethyl acetate/heptane 20:80) to yield 16.8 g of impure material containing unreacted naphthylmethanol. The material was repurified (Aminophase, 0% to 35% ethylacetate in heptane gradient) to yield 11.1 g (52%) of the title compound as a white crystalline solid, MS: m/e=314.2 (M+H$^+$).

Step 2: (rac)-(1SR,2RS)-2-(Naphthalen-2-yl-methoxycarbonylamino)cyclobutanecarboxylic Acid To a well stirred solution of (rac)-(1SR,2RS)-2-(naphthalen-2-ylmethoxycarbonylamino) cyclobutanecarboxylic acid methyl ester (Example 1, step 1) (4.2 g, 13.4 mmol), in 20 ml of dioxane was added water (70 ml). The solution was cooled to 5° C. and 53.6 ml (26.8 mmol) of 0.5M sodium hydroxide solution were added dropwise over a period of 5 min. After stirring for 1 h at 5° C., the reaction was allowed to warm up to room temperature with vigourous stirring. The clear solution was then cooled to 5° C. and the pH was adjusted to 2.5 by addition of ca. 13 ml 2N hydrochloric acid solution. The reaction was worked up with ethyl acetate. After drying, filtration and concentration in vaccuo, 3.87 g (97%) of the title compound was obtained as a crystalline white solid, MS: m/e=300.2 (M+H$^+$).

Step 3: (rac)-(1RS,5SR)-3-Oxo-2,4-diaza-bicyclo[3.2.0]heptane-2-carboxylic Acid naphthalen-2-ylm-ethyl Ester A solution of (rac)-(1SR,2RS)-2-(naphthalen-2-yl-methoxycarbonylamino)cyclobutanecarboxylic acid (Example 1, step 2) (2.34 g, 7.82 mmol) and N-methylmorpholine (0.79 g, 0.86 ml, 7.82 mmol) in 34 ml of dichloroethane was stirred at r.t. for 10 min. Then diphenylphosphoricacid azide (2.15 g, 1.69 ml, 7.82 mmol) was added dropwise at room temperature and the colorless solution was stirred for 1 h at room temperature during which the solution turned light yellow. The solution was then warmed to 50° C., stirred for 6 h and allowed to cool. After workup with dichloromethane/water, the combined organic phases were evaporated to dryness to yield a yellow solid which was recristallized from ethyl acetate/heptane. The title compound (1.86 g, 80%) was obtained as a white crystalline solid, MS: m/e=297.3 (M+H$^+$).

Step 4: (rac)-(1RS,5SR)-4-Methyl-3-oxo-2,4-diaza-bicyclo[3.2.0]heptane-2-carboxylic Acid naphthalen-2-ylmethyl Ester To a solution of (rac)-(1RS,5SR)-3-Oxo-2,4-diaza-bicyclo[3.2.0]heptane-2-carboxylic acid naphthalen-2-ylmethyl ester (Example 1, step 3) (1.13 g, 3.81 mmol) in 11 ml of DMF was added a 60% suspension of sodium hydride in mineral oil (0.198 g, 4.96 mmol). The suspension was stirred for 35 minutes at room temperature (gas evolution), then iodomethane (0.81 g, 0.36 ml, 5.72 mmol) was added and the mixture was stirred at room temperature overnight. After quenching by addition of 3 ml sat. ammonium chloride solution and concentration in vaccuo, the residue was worked up with ethyl acetate/water. The combined organic phases were dried and concentrated in vaccuo. The residue was purified by flash chromatography on silicagel (50 g) eluting with a 20-100% ethyl acetate in heptane gradient to yield 0.98 g (82%) of a colorless oil, MS: m/e=311.2 (M+H$^+$).

Step 5: (rac)-(1SR,5RS)-2-Methyl-2,4-diaza-bicyclo[3.2.0]heptan-3-one

A solution of (rac)-(1RS,5SR)-4-Methyl-3-oxo-2,4-diaza-bicyclo[3.2.0]heptane-2-carboxylic acid naphthalen-2-ylm-ethyl ester (Example 1, step 4) (0.97 g, 3.13 mmol) in 15 ml of methanol was hydrogenated for 48 h over 10% Pd/C (0.333 g, 0.313 mmol). The solution was purged with argon, the catalyst was filtered off and washed with ethyl acetate. The filtrate was concentrated in vaccuo. The residue was purified by flash chromatography on silicagel (20 g) eluting with a 50-100% ethyl acetate in heptane gradient to yield 0.375 g (95%) of the title compound as a crystalline white solid, which was directly used in the next step without further characterisation.

Step 6: (rac)-(1RS,5SR)-2-(5-Iodo-pyridin-2-yl)-4-methyl-2,4-diaza-bicyclo[3.2.0]heptan-3-one To a solution of (rac)-(1SR,5RS)-2-methyl-2,4-diaza-bi-cyclo[3.2.0]heptan-3-one (Example 1, step 5) (375 mg, 2.97 mmol) and 2-fluoro-5-iodopyridine (683 mg, 3.06 mmol) in DMF (10 ml) was added a 60% suspension of sodium hydride in mineral oil (155 mg, 3.86 mmol). The reaction was stirred at room temperature overnight. After quenching by addition of 3 ml sat. ammonium chloride solution and concentration in vaccuo to eliminate the DMF, the residue was worked up with ethyl acetate/water. After drying and concentration in vaccuo, the residue was purified by flash chromatography (SiO$_2$, 20 g) using a 0% to 65% ethyl acetate in heptane gradient. One obtains the title compound, (549 mg, 56%), as a crystalline white solid, MS: m/e=330.1 (M+H$^+$).

Step 7: (rac)-(+/−)-(1SR,5RS)-2-Methyl-4-(5-(phe-nylethynyl)pyridin-2-yl)-2,4-diazabicyclo[3.2.0]heptan-3-one In a 5 ml microwave tube were dissolved 110 mg (0.33 mmol) of (rac)-(1RS,5SR)-2-(5-iodo-pyridin-2-yl)-4-methyl-2,4-diaza-bicyclo[3.2.0]heptan-3-one (Example 1, step 6) in 1.5 ml DMF. Argon was bubbled through the solution. Ethynylbenzene (73 μl, 68 mg, 0.67 mmol), Bis (triphenylphosphine)palladium(II) chloride (14 mg, 20 μmol), copper (I) iodide (1.9 mg, 10.0 μmol), Triph-enylphosphine (1.8 mg, 7.7 μmol) and 107 μl of Triethyl-amine (101 mg, 140 μl, 1.0 mmol) were added. The dark brown solution was stirred 3 h at 60° C. The reaction was worked up with ethyl acetate/water, dried and concentrated in vaccuo. The residue was purified by flash chromatography (silica gel, 20 g, 0% to 50% EtOAc in heptane gradient) to yield 95 mg (94%) of the title compound as a light brown crystalline solid, MS: m/e=304.2 (M+H$^+$).

Step 8: (−)-(1S,5R)-2-Methyl-4-(5-(phenylethynyl)pyridin-2-yl)-2,4-diazabicyclo[3.2.0]heptan-3-one and (+)-(1R,5S)-2-methyl-4-(5-(phenylethynyl)pyri-din-2-yl)-2,4-diazabicyclo[3.2.0]heptan-3-one The racemic mixture of (rac)-(+/−)-(1SR,5RS)-2-methyl-4-(5-(phenylethynyl)pyridin-2-yl)-2,4-diazabicyclo[3.2.0]heptan-3-one (Example 1, step 7) (95 mg) was separated by chiral HPLC: (Chiralpak AD®-5 cm×50 cm, 20 mM; 40% isopropanol/heptane, 35 ml/min, 18 Bar). Peak detection was realized using a UV-detector as well as an optical rotation detector (ORD) where one peak has a negative signal (the (−)-enantiomer), and the other peak has a positive signal (the (+)-enantiomer). The (−)-enantiomer, (−)-(1S, 5R)-2-methyl-4-(5-(phenylethynyl)pyridin-2-yl)-2,4-diazabicyclo[3.2.0]heptan-3-one (39 mg) was obtained as a crystalline light yellow solid, MS: m/e=304.1 (M+H⁺). The (+)-enantiomer, (−)-(1R,5S)-2-methyl-4-(5-(phenylethynyl)pyridin-2-yl)-2,4-diazabicyclo[3.2.0]heptan-3-one (40 mg) was obtained as a light yellow solid, MS: m/e=304.1 (M+H⁺).

Example 2

(−)-(1R,5S)-2-[5-(3-Fluoro-phenylethynyl)-pyridin-2-yl]-4-methyl-2,4-diazabicyclo [3.2.0]heptan-3-one

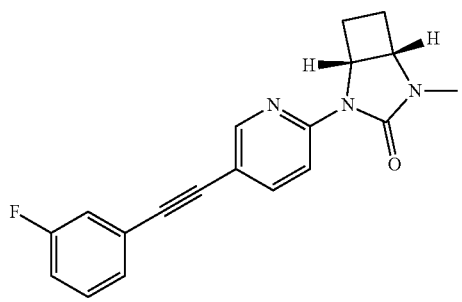 [SMILES: CN1C(=O)N(c2ccc(C#Cc3cccc(F)c3)cn2)[C@@H]2CC[C@@H]21]

The title compound was prepared in accordance with the general method of Example 1, step 7 starting from (rac)-(1RS,5SR)-2-(5-iodo-pyridin-2-yl)-4-methyl-2,4-diaza-bicyclo[3.2.0]heptan-3-one (Example 1, step 6) (110 mg) and 1-ethynyl-3-fluorobenzene to yield 107 mg (96%) of racemic material ((+/−)-(1R,5S)-2-[5-(3-fluoro-phenylethynyl)-pyridin-2-yl]-4-methyl-2,4-diazabicyclo[3.2.0]heptan-3-one as a light yellow crystalline solid; MS: m/e=322.3 (M+H⁺) which was then separated by chiral HPLC using similar separation conditions as described in example 1, step 8 to yield the enantiomerically pure enantiomers (−)-(1R,5S)-2-[5-(3-fluoro-phenylethynyl)-pyridin-2-yl]-4-methyl-2,4-diazabicyclo[3.2.0]heptan-3-one as a light yellow solid, MS: m/e=322.3 (M+H⁺); and its enantiomer (+)-(1S,5R)-2-[5-(3-fluoro-phenylethynyl)-pyridin-2-yl]-4-methyl-2,4-diazabicyclo[3.2.0]heptan-3-one as a light yellow solid; MS: m/e=322.3 (M+H⁺).

Example 3

(−)-(1R,5S)-2-[5-(4-Fluoro-phenylethynyl)-pyridin-2-yl]-4-methyl-2,4-diazabicyclo[3.2.0]heptan-3-one

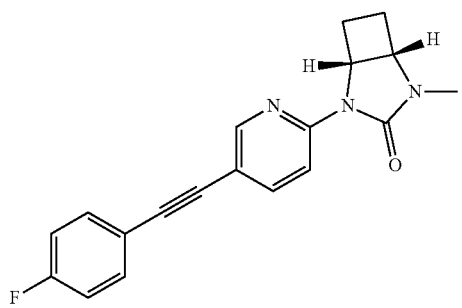 [SMILES: CN1C(=O)N(c2ccc(C#Cc3ccc(F)cc3)cn2)[C@@H]2CC[C@@H]21]

The title compound was prepared in accordance with the general method of Example 1, step 7 starting from (rac)-(1RS,5SR)-2-(5-iodo-pyridin-2-yl)-4-methyl-2,4-diaza-bicyclo[3.2.0]heptan-3-one (Example 1, step 6) (110 mg) and 1-ethynyl-4-fluorobenzene to yield 104 mg (97%) of racemic material ((+/−)-(rac)-(1SR,5RS)-2-[5-(4-fluoro-phenylethynyl)-pyridin-2-yl]-4-methyl-2,4-diazabicyclo[3.2.0]heptan-3-one as a light yellow crystalline solid; MS: m/e=322.3 (M+H⁺) which was then separated by chiral HPLC using similar separation conditions as described in example 1, step 8 to yield the enantiomerically pure enantiomers (−)-(1R,5S)-2-[5-(4-fluoro-phenylethynyl)-pyridin-2-yl]-4-methyl-2,4-diazabicyclo[3.2.0]heptan-3-one as a light yellow solid, MS: m/e=322.3 (M+H⁺); and its enantiomer (+)-(1S,5R)-2-[5-(4-fluoro-phenylethynyl)-pyridin-2-yl]-4-methyl-2,4-diazabicyclo[3.2.0]heptan-3-one as a light yellow solid; MS: m/e=322.3 (M+H⁺).

Example 4

(−)-(1R,5S)-2-[5-(2,5-Difluoro-phenylethynyl)-pyridin-2-yl]-4-methyl-2,4-diazabicyclo[3.2.0]heptan-3-one

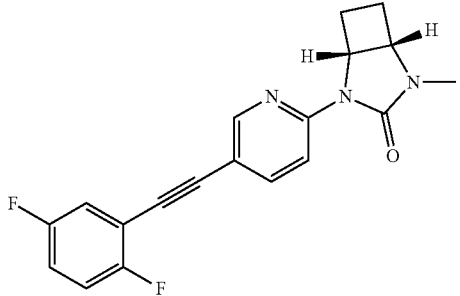 [SMILES: CN1C(=O)N(c2ccc(C#Cc3cc(F)ccc3F)cn2)[C@@H]2CC[C@@H]21]

The title compound was prepared in accordance with the general method of Example 1, step 7 starting from (rac)-(1RS,5SR)-2-(5-iodo-pyridin-2-yl)-4-methyl-2,4-diaza-bicyclo[3.2.0]heptan-3-one (Example 1, step 6) (110 mg) and 2-ethynyl-1,4-difluorobenzene to yield 110 mg (97%) of racemic material ((+/−)-(rac)-(1SR,5RS)-2-[5-(2,5-difluoro-phenylethynyl)-pyridin-2-yl]-4-methyl-2,4-diazabicyclo [3.2.0]heptan-3-one as a light yellow crystalline solid; MS: m/e=340.1 (M+H⁺) which was then separated by chiral HPLC using similar separation conditions as described in example 1, step 8 to yield the enantiomerically pure enantiomers (−)-(1R,5S)-2-[5-(2,5-difluoro-phenyl-ethynyl)-pyridin-2-yl]-4-methyl-2,4-diazabicyclo[3.2.0]heptan-3-one as a light yellow solid, MS: m/e=340.1 (M+H⁺); and its enantiomer (+)-(1S,5R)-2-[5-(2,5-difluoro-phenyl-ethynyl)-pyridin-2-yl]-4-methyl-2,4-diazabicyclo[3.2.0]heptan-3-one as a light yellow solid; MS: m/e=340.1 (M+H⁺).

| Preparation of the pharmaceutical compositions: |  |
| --- | --- |
| Example I Tablets of the following composition are produced in a conventional manner: | |
|  | mg/Tablet |
| Active ingredient | 100 |
| Powdered lactose | 95 |

-continued

| Preparation of the pharmaceutical compositions: | |
|---|---|
| White corn starch | 35 |
| Polyvinylpyrrolidone | 8 |
| Na carboxymethylstarch | 10 |
| Magnesium stearate | 2 |
| Tablet weight | 250 |

Example II
Tablets of the following composition are
produced in a conventional manner:

| | mg/Tablet |
|---|---|
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

Example III
Capsules of the following composition are produced:

| | mg/Capsule |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

The invention claimed is:

1. A compound selected from the group consisting of:
    (1R,5S)-2-methyl-4-(5-(phenylethynyl)pyridin-2-yl)-2,4-diazabicyclo[3.2.0]heptan-3-one;
    (1S,5R)-2-(5-((4-fluorophenyl) ethynyl)pyridin-2-yl)-4-methyl-2,4-diazabicyclo[3.2.0]heptan-3-one;
    (1S,5R)-2-(5-((3-fluorophenyl) ethynyl)pyridin-2-yl)-4-methyl-2,4-diazabicyclo[3.2.0]heptan-3-one; and
    (1S,5R)-2-(5-((2,5-difluorophenyl) ethynyl)pyridin-2-yl)-4-methyl-2,4-diazabicyclo[3.2.0]heptan-3-one;
    or a pharmaceutically acceptable salt thereof.

2. The compound of claim 1, wherein the compound is (1R,5S)-2-methyl-4-(5-(phenylethynyl)pyridin-2-yl)-2,4-diazabicyclo[3.2.0]heptan-3-one, or a pharmaceutically acceptable salt thereof.

3. The compound of claim 1, wherein the compound is (1S,5R)-2-(5-((4-fluorophenyl) ethynyl)pyridin-2-yl)-4-methyl-2,4-diazabicyclo[3.2.0]heptan-3-one, or a pharmaceutically acceptable salt thereof.

4. The compound of claim 1, wherein the compound is (1S,5R)-2-(5-((3-fluorophenyl) ethynyl)pyridin-2-yl)-4-methyl-2,4-diazabicyclo[3.2.0]heptan-3-one, or a pharmaceutically acceptable salt thereof.

5. The compound of claim 1, wherein the compound is (1S,5R)-2-(5-((2,5-difluorophenyl) ethynyl)pyridin-2-yl)-4-methyl-2,4-diazabicyclo[3.2.0]heptan-3-one, or a pharmaceutically acceptable salt thereof.

6. A pharmaceutical composition comprising a compound of claim 1, or a pharmaceutically acceptable salt thereof, and a therapeutically inert excipient.

7. The pharmaceutical composition of claim 6, wherein the compound of the composition is (1R,5S)-2-methyl-4-(5-(phenylethynyl)pyridin-2-yl)-2,4-diazabicyclo[3.2.0]heptan-3-one, or a pharmaceutically acceptable salt thereof.

8. The pharmaceutical composition of claim 6, wherein the compound of the composition is (1S,5R)-2-(5-((4-fluorophenyl) ethynyl)pyridin-2-yl)-4-methyl-2,4-diazabicyclo[3.2.0]heptan-3-one, or a pharmaceutically acceptable salt thereof.

9. The pharmaceutical composition of claim 6, wherein the compound of the composition is (1S,5R)-2-(5-((3-fluorophenyl) ethynyl)pyridin-2-yl)-4-methyl-2,4-diazabicyclo[3.2.0]heptan-3-one, or a pharmaceutically acceptable salt thereof.

10. The pharmaceutical composition of claim 6, wherein the compound of the composition is (1S,5R)-2-(5-((2,5-difluorophenyl) ethynyl)pyridin-2-yl)-4-methyl-2,4-diazabicyclo[3.2.0]heptan-3-one, or a pharmaceutically acceptable salt thereof.

11. A method for the treatment of anxiety, pain, depression, Fragile-X syndrome, an autism spectrum disorder, Parkinson's disease, or gastro-esophageal reflux disease (GERD) in a patient, the method comprising administering to the patient in need thereof an effective amount of a compound of claim 1, or a pharmaceutically acceptable salt thereof.

12. The method of claim 11, wherein the administered compound is (1R,5S)-2-methyl-4-(5-(phenylethynyl)pyridin-2-yl)-2,4-diazabicyclo[3.2.0]heptan-3-one, or a pharmaceutically acceptable salt thereof.

13. The method of claim 11, wherein the administered compound is (1S,5R)-2-(5-((4-fluorophenyl) ethynyl)pyridin-2-yl)-4-methyl-2,4-diazabicyclo[3.2.0]heptan-3-one, or a pharmaceutically acceptable salt thereof.

14. The method of claim 11, wherein the administered compound is (1S,5R)-2-(5-((3-fluorophenyl) ethynyl)pyridin-2-yl)-4-methyl-2,4-diazabicyclo[3.2.0]heptan-3-one, or a pharmaceutically acceptable salt thereof.

15. The method of claim 11, wherein the administered compound is (1S,5R)-2-(5-((2,5-difluorophenyl) ethynyl)pyridin-2-yl)-4-methyl-2,4-diazabicyclo[3.2.0]heptan-3-one, or a pharmaceutically acceptable salt thereof.

* * * * *